US009707076B2

(12) United States Patent
Stack et al.

(10) Patent No.: US 9,707,076 B2
(45) Date of Patent: Jul. 18, 2017

(54) DIRECT AORTIC ACCESS SYSTEM FOR TRANSCATHETER AORTIC VALVE PROCEDURES

(71) Applicant: Synecor LLC, Chapel Hill, NC (US)

(72) Inventors: Richard S Stack, Chapel Hill, NC (US); Richard A Glenn, Chapel Hill, NC (US); Michael S Williams, Santa Rosa, CA (US); William L Athas, Chapel Hill, NC (US)

(73) Assignee: MINIMALLY INVASIVE SURGICAL ACCESS LIMITED, Dublin (IE)

( * ) Notice: Subject to any disclaimer, the term of this patent is extended or adjusted under 35 U.S.C. 154(b) by 415 days.

(21) Appl. No.: 13/975,258

(22) Filed: Aug. 23, 2013

(65) Prior Publication Data

US 2014/0222031 A1    Aug. 7, 2014

Related U.S. Application Data

(60) Provisional application No. 61/692,702, filed on Aug. 23, 2012, provisional application No. 61/703,165,
(Continued)

(51) Int. Cl.
*A61F 2/24* (2006.01)
*A61F 2/01* (2006.01)
(Continued)

(52) U.S. Cl.
CPC ........ *A61F 2/2427* (2013.01); *A61B 17/0483* (2013.01); *A61B 17/062* (2013.01);
(Continued)

(58) Field of Classification Search
CPC ... A61F 2/2427; A61B 17/34; A61B 17/3415; A61B 17/3421; A61B 17/3468
See application file for complete search history.

(56) References Cited

U.S. PATENT DOCUMENTS 5,676,636 A    10/1997 Chin
5,980,503 A    11/1999 Chin
(Continued)

FOREIGN PATENT DOCUMENTS

WO    0018303 A1    4/2000

OTHER PUBLICATIONS

Webb, J.G. et al, "Current status of transcatheter aortic valve replacement" Journal of the American College of Cardiology, Aug. 7, 2012, vol. 60, No. 6, 483-492.
(Continued)

*Primary Examiner* — Todd J Scherbel

(57) ABSTRACT

Disclosed are a system and method for performing a medical procedure using direct percutaneous access of an aorta. A main sheath is introduced through an incision formed in proximity to the sternum, and positioned along (and preferable against) a posterior portion of the sternum. Instruments passed through the main sheath are used to form a purse-string suture in an exterior wall of the aorta. An opening is formed in the wall of the aorta in a region encircled by the purse-string suture, and a distal end of an introducer sheath is advanced through the opening into the aorta. A medical procedure, which may be a transcatheter aortic valve replacement, is performed using instruments passed through the introducer sheath into the aorta. After the medical procedure, the introducer sheath is withdrawn from the aorta and, as the introducer sheath is withdrawn, the purse-string suture is tightened to close the opening.

7 Claims, 16 Drawing Sheets

Related U.S. Application Data filed on Sep. 19, 2012, provisional application No. 61/728,679, filed on Nov. 20, 2012.

(51) Int. Cl.
  *A61B 17/04* (2006.01)
  *A61B 17/34* (2006.01)
  *A61B 17/062* (2006.01)
  *A61M 39/06* (2006.01)
  *A61M 25/04* (2006.01)
  *A61B 17/00* (2006.01)
  *A61B 17/29* (2006.01)
  *A61B 17/30* (2006.01)
  *A61B 90/00* (2016.01)

(52) U.S. Cl.
  CPC .......... *A61B 17/3421* (2013.01); *A61F 2/013* (2013.01); *A61M 39/0613* (2013.01); *A61B 17/0469* (2013.01); *A61B 90/361* (2016.02); *A61B 2017/00243* (2013.01); *A61B 2017/00252* (2013.01); *A61B 2017/00278* (2013.01); *A61B 2017/2927* (2013.01); *A61B 2017/306* (2013.01); *A61B 2017/3425* (2013.01); *A61B 2017/3445* (2013.01); *A61M 25/04* (2013.01); *A61M 2039/0626* (2013.01); *A61M 2039/0673* (2013.01)

(56) References Cited

U.S. PATENT DOCUMENTS

| | | | |
|---|---|---|---|
| 6,402,780 B2 | 6/2002 | Williamson, IV et al. | |
| 6,651,671 B1 * | 11/2003 | Donlon et al. | 128/898 |
| 6,830,584 B1 | 12/2004 | Seguin | |
| 6,896,690 B1 | 5/2005 | Lambrecht et al. | |
| 6,929,653 B2 | 8/2005 | Strecter | |
| 7,201,761 B2 | 4/2007 | Woolfson et al. | |
| RE40,377 E | 6/2008 | Williamson, IV et al. | |
| 7,470,284 B2 | 12/2008 | Lambrecht et al. | |
| 7,544,206 B2 | 6/2009 | Cohn | |
| 7,749,205 B2 | 7/2010 | Tazoe et al. | |
| 8,808,369 B2 | 8/2014 | Suri | |
| 2003/0233108 A1 | 12/2003 | Gellman et al. | |
| 2009/0112285 A1 | 4/2009 | Cahan et al. | |
| 2010/0179647 A1 * | 7/2010 | Carpenter et al. | 623/2.11 |
| 2010/0312069 A1 | 12/2010 | Sutherland et al. | |
| 2011/0282286 A1 | 11/2011 | Argentine | |
| 2012/0037686 A1 | 2/2012 | Hessler | |
| 2013/0267785 A1 | 10/2013 | Sutherland et al. | |

OTHER PUBLICATIONS

International Search Report for PCT/US2013/056530, WO 2014/032035.
Cosgrove III, Delos M. et al, Minimally Invasive Approach for Aortic Valve Operations, Ann Thorac Surg 1996; 62:596-7.
Philipsen, Tine E. et al, Alternative Access in Transcatheter Aortic Valve Implantation: Brachiocephalic Artery Access, Innovations 7: 372-375 2012.
Ramlawi, Basel et al, Transcatheter Aortic Valve Replacement (TAVR): Access Planning and Strategies, Methodist DeBakey Cardiovascular Journal, VIII(2) 2012.

* cited by examiner

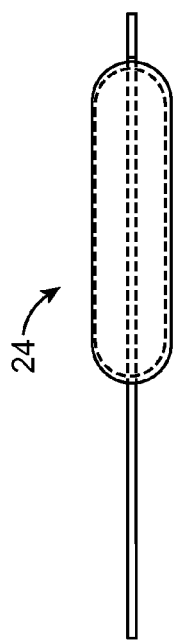
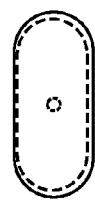
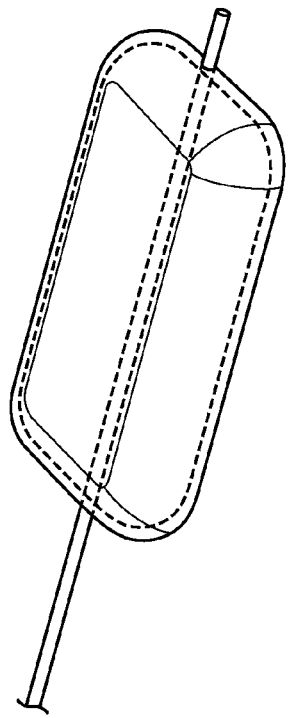
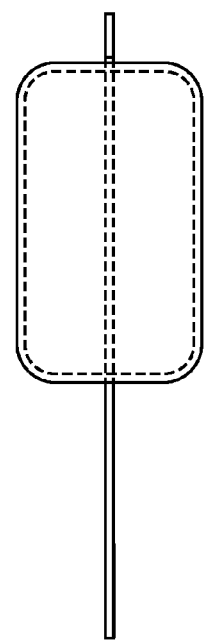
FIG. 14A
FIG. 14B
FIG. 14C
FIG. 14D

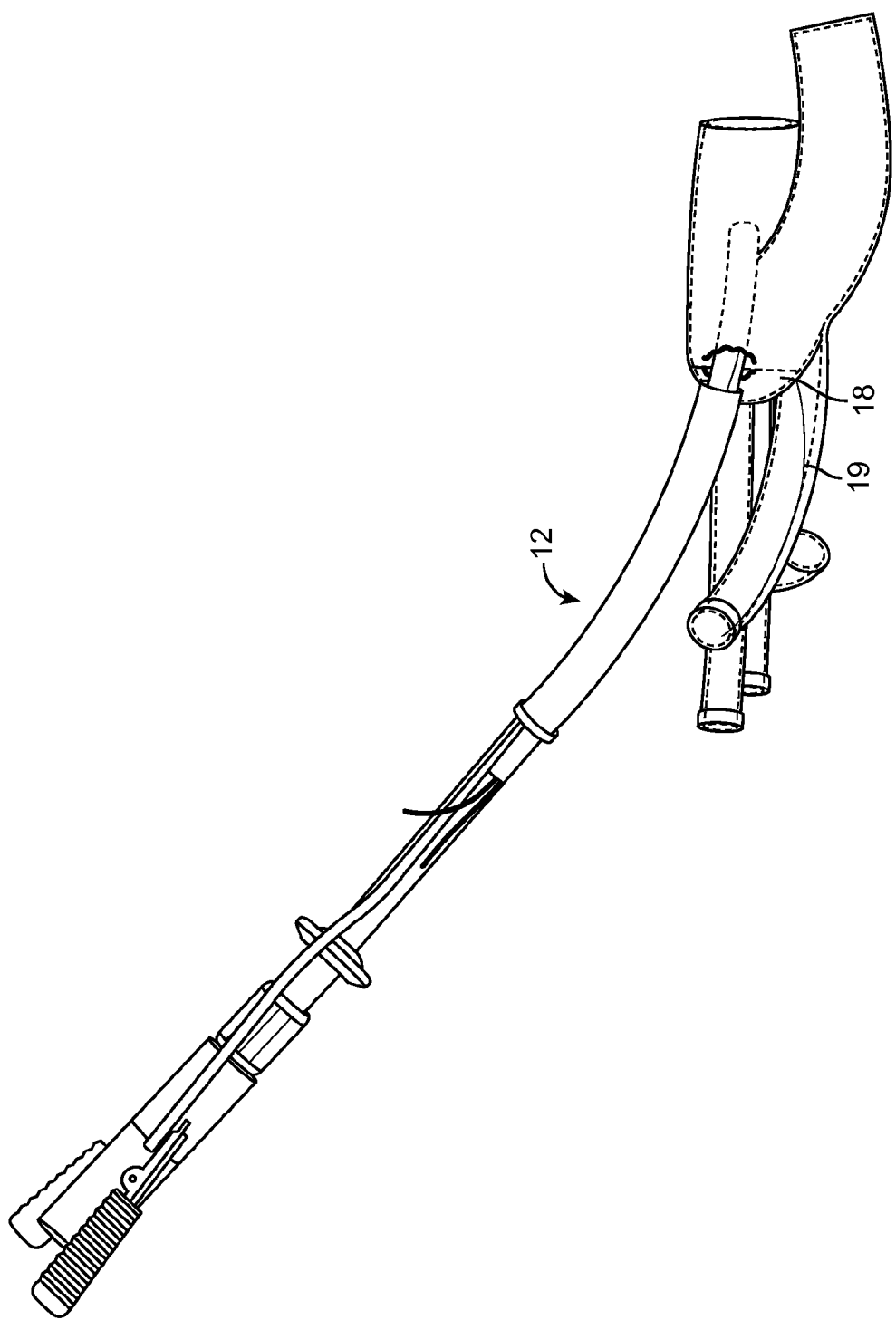

DIRECT AORTIC ACCESS SYSTEM FOR TRANSCATHETER AORTIC VALVE PROCEDURES

This application claims priority to U.S. Provisional Application No. 61/692,702, filed 23 Aug. 2012, U.S. Provisional Application No. 61/702,165, filed 19 Sep. 2012, and U.S. Provisional Application No. 61/728,679, filed 20 Nov. 2012, each of which is incorporated herein by reference.

FIELD OF THE INVENTION

The field of the invention relates generally to the field of percutaneous access systems, and more specifically to the field of percutaneous systems for direct percutaneous access to the aorta.

BACKGROUND

Transcatheter aortic-valve implantation (TAVI) has emerged as a therapeutic option to improve symptoms and extend life in high-risk patients with severe symptomatic Aortic Stenosis.

Various approaches have been described for accessing the aortic valve during the TAVI procedure. One TAVI approach is a transfemoral (TF) route in which catheters are guided through the aorta and retrograde across the diseased valve.

A second approach, the direct transaortic (TAo) route, mimics the TF route but avoids passing instruments along the curvature of manipulating the aortic arch, reducing the risk of embolization. While TAo-TAVI is currently performed through an upper ministernotomy or a right minithoracotomy, the aortic anatomy is such that the ascending aorta could be accessed percutaneously from just above the suprasternal notch. The ascending aorta would be pierced and cannulated. In some embodiments, cannulation might occur at the level of the second intercostal cartilage, where it lies anteromedial to the superior vena cava, although other sites might also be used.

The transition from surgical or vascular access to a direct percutaneous approach has the potential to reduce the requirement for general anesthesia, shorten procedure time, reduce the risk of wound infections, mitigate patient discomfort, reduce post-op patient immobilization, and shorten length of hospitalization. To realize the potential of percutaneous transaortic (pTAo) TAVI, however, new tools are needed for access, embolic protection, and closure.

BRIEF DESCRIPTION OF THE DRAWINGS

FIGS. 14A-D show a side elevation view, distal plan view, top plan view, and perspective view, respectively, of a thoracic dissection balloon.

FIG. 17 is a side view illustrating the curvature of the main sheath of FIG. 6.

DETAILED DESCRIPTION

This application discloses a system for facilitating percutaneous access directly into the aorta. As disclosed in the application, the system is particularly suitable for use in gaining access to the aortic valve for treatment. For example, the system can be used to give access to devices and instruments used for implantation of an artificial aortic valve (e.g. TAVI procedures). The system is proportioned to allow the artificial aortic valve and its delivery system to be positioned through it during the valve implantation procedure.

System

Figure 1:
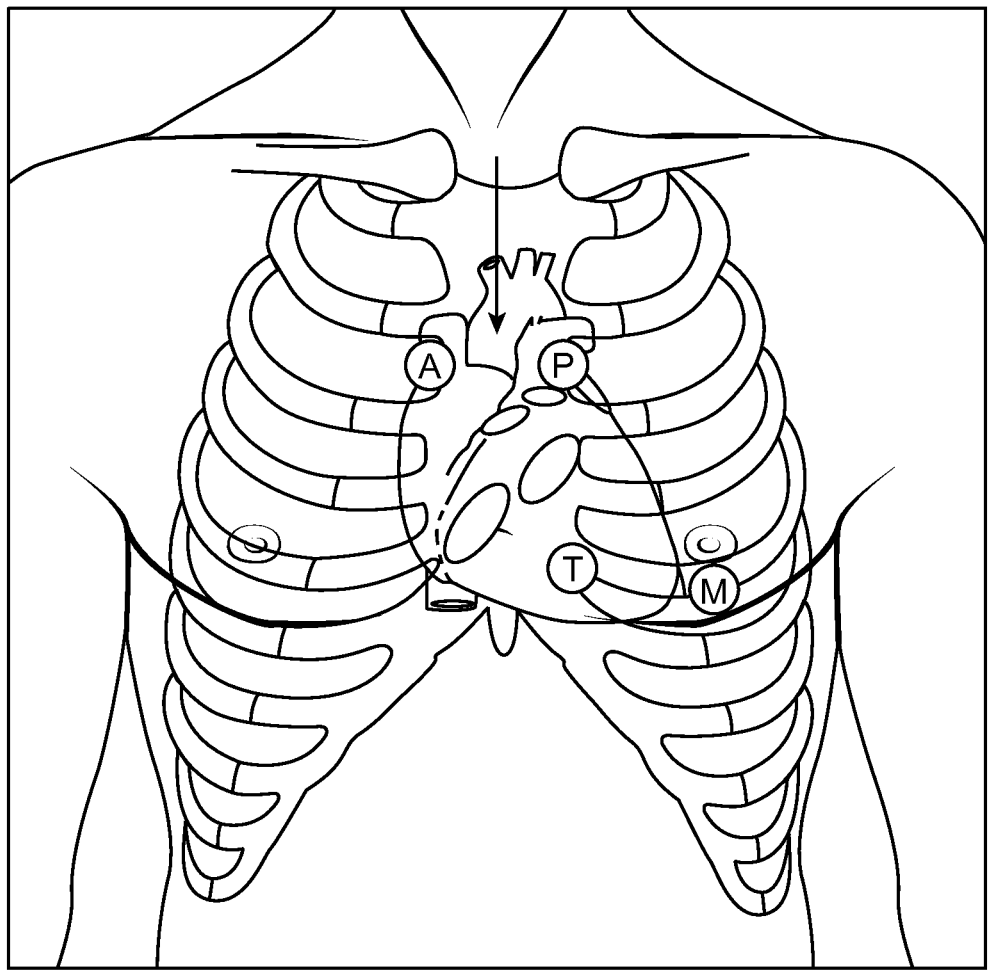
FIG. 1 schematically illustrates access to the aorta using the disclosed percutaneous transaortic approach.

FIG. 1 schematically illustrates the access approach for which the system may be used. In particular, direct percutaneous access into the aorta is gained by forming an incision above the suprasternal notch and approaching the aorta as indicted by the illustrated arrow. The access system is introduced through the incision and positioned behind the sternum, giving access to the aorta as indicated by the arrow in FIG. 1. Additional details of an exemplary method for using the system are described following the description of the system components.

Main Sheath

Figure 2:
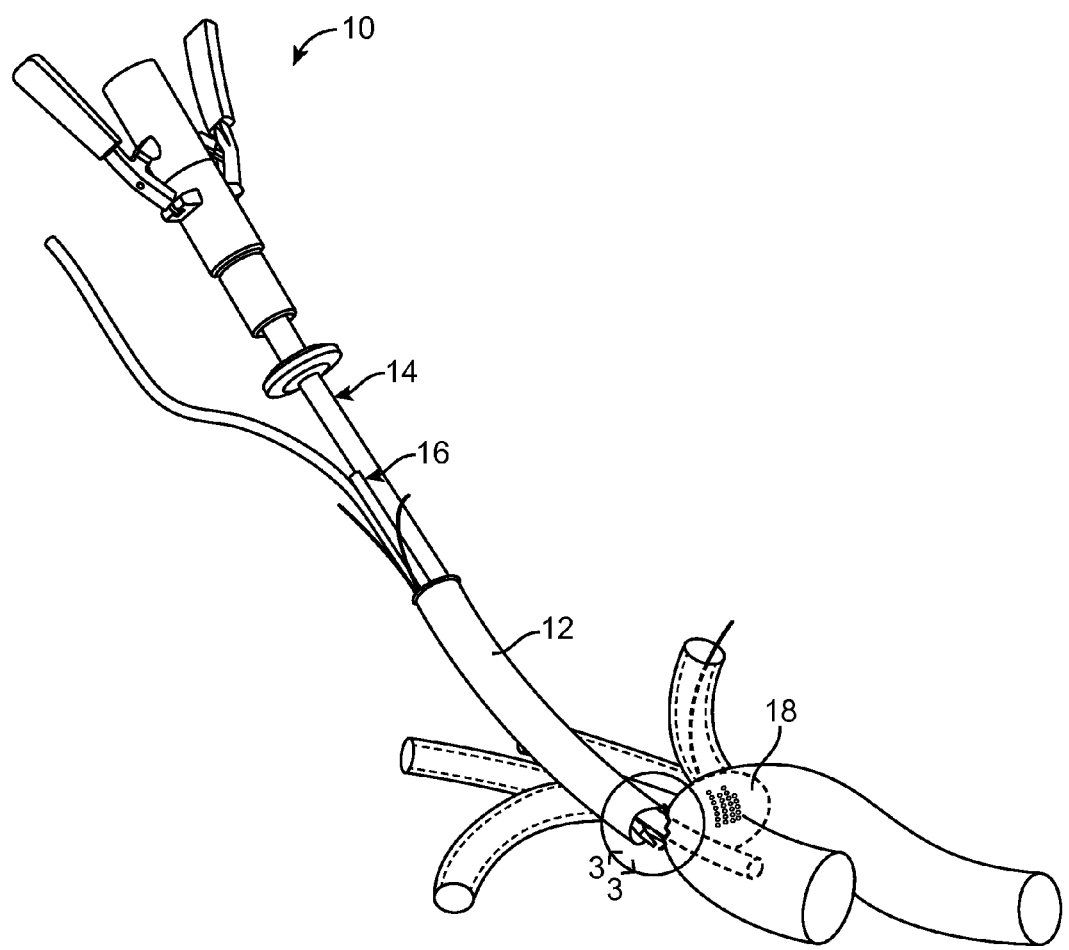
FIG. 2 schematically illustrates an aorta and shows components of the disclosed transaortic access system accessing the aorta.

Referring to FIG. 2, an aortic access system 10 includes a main sheath 12, an introducer sheath 14 extendable through the main sheath 12, and a purse-string suture applier 16 also extendable through the main sheath. Additional components which might also be included in the system 10, including an embolic protection device 18, obturator 20, and dissection balloons 22, 24 are also shown in the drawings and will be described below.

Figure 6:
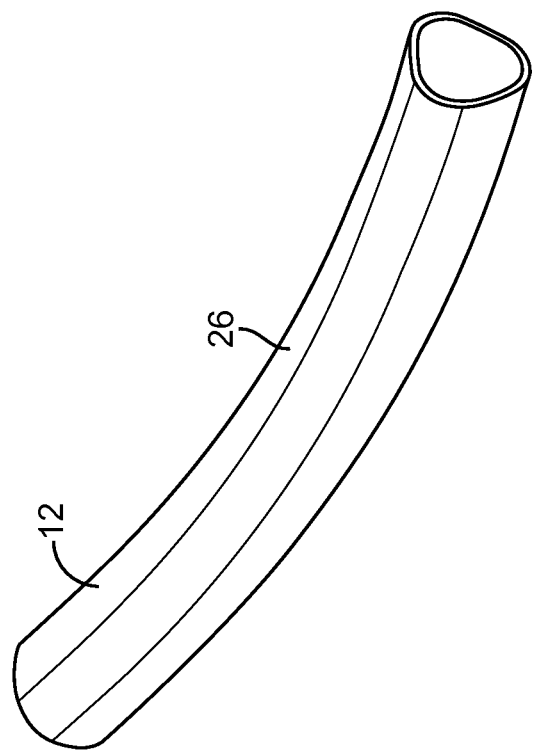
FIG. 6 is a perspective view of the main sheath of FIG. 5.

An exemplary main sheath 12 is shown in FIG. 6. The main sheath functions to provide an access way through the skin and to accommodate the introducer sheath 14, purse-string suture applier 15 and scope in stable positions in a manner that avoids "sword fighting" between the instruments, yet preferably allows enough freedom of movement of the introducer sheath to move side-to-side if needed.

Main sheath 12 is an elongate tubular sheath having a lumen extending between its proximal and distal ends. The main sheath 12 preferably has a cross-section that is non-circular so as to include a face 26 or flattened region shaped to seat against the posterior face of the sternum when the main sheath 12 is disposed behind the sternum. The main sheath 12 of the FIG. 6 embodiment has a generally triangular cross-section, with the corner regions preferably rounded so as to avoid tissue trauma. The illustrated cross-section is equilateral although other geometries can be used. With this arrangement, the main sheath 12 has three generally rectangular faces, allowing any of the faces to seat against the sternum (or against soft tissue that is behind the sternum).

In the FIG. 6 embodiment, the main sheath 12 has a preformed curve such that, when the distal portion of the main sheath is within the body, its proximal portion curves away from the plane of the operating table (with the patient in a supine position) and thus away from the patient's head. See FIGS. 16 and 17.

Figure 10:
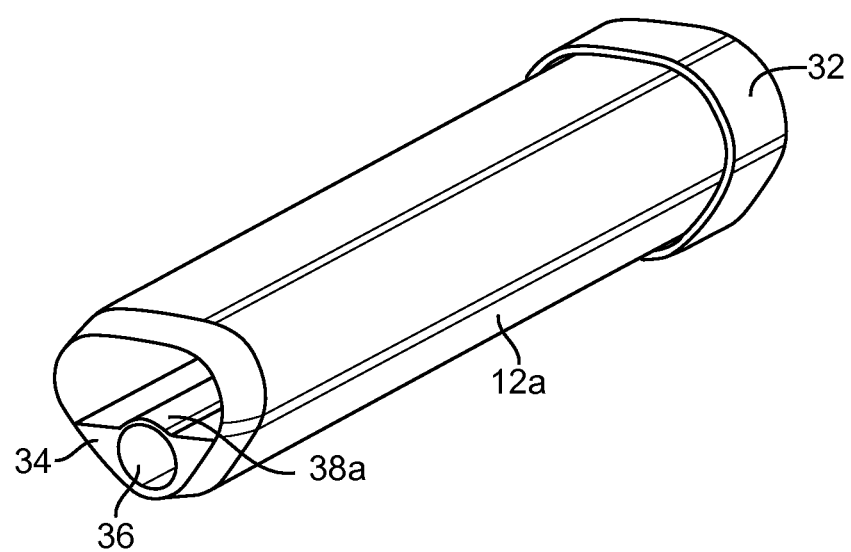
FIG. 10 is a perspective view of an alternative to the main sheath of FIG. 6, with the insert assembly positioned within the sheath.

An alternative main sheath 12a, shown in FIG. 10, is longitudinally straight, giving the sheath the shape of a triangular prism with rounded edges. The distal end of any of the disclosed main sheaths may include a chamfered or tapered edge as shown in FIG. 10 so as a minimize tissue trauma when the main sheath is advanced into the body. The straight main sheath 12a may have a length that is approximately 3 inches or less or 2 inches or less, so as to avoid conflict with the patient's head as instruments are passed into the proximal end of the main sheath 12a.

Figure 11B:
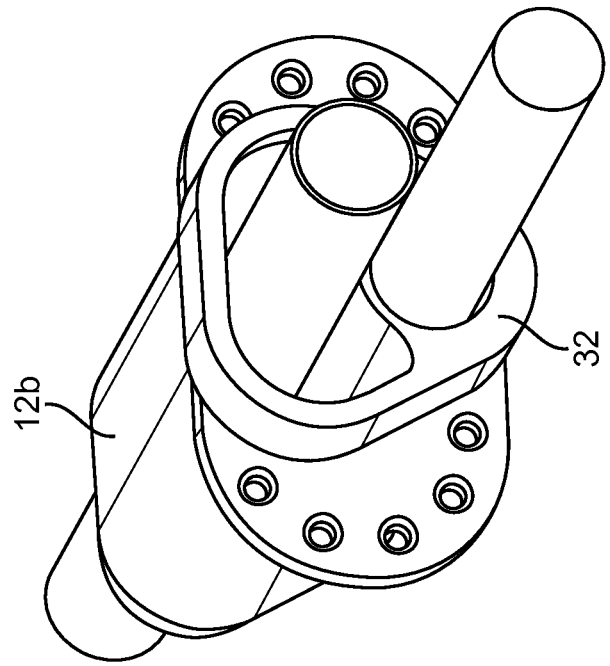
FIG. 11B is a proximal perspective view of the assembly of FIG. 11A. The distal portions of the introducer sheath and an endoscope are shown disposed in the main sheath.
Figure 11A:
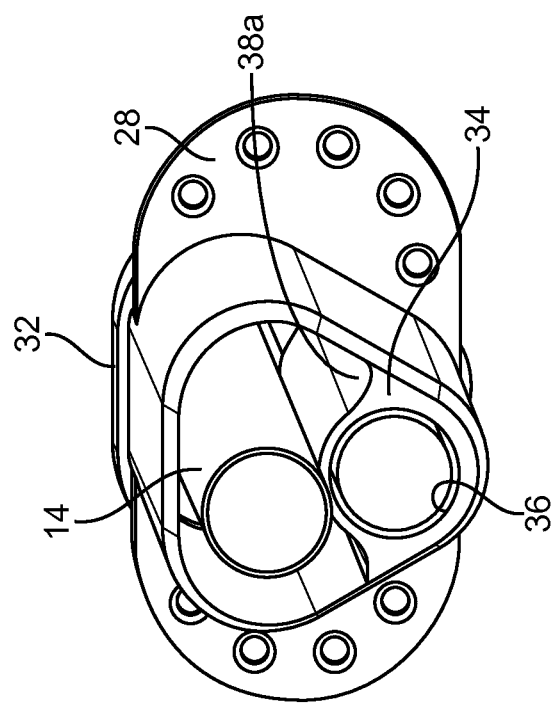
FIG. 11A is a distal perspective view of a second alternative main sheath, with the insert positioned within the sheath.

A third main sheath 12b is shown in FIGS. 11A and 11B. This sheath is similar to the main sheath 12a, but further includes flanges 28 as shown. The flanges 28 include tie-down holes that receive sutures (not shown). During use, sutures are passed through the tie-down holes and the patient's skin so as to temporarily couple the main sheath 12b to the patient.

Although main sheaths with triangular cross-sections are shown, alternative main sheaths may have other cross-sectional shapes. Preferred shapes are those which include an outer face shaped to seat against the back of the sternum (or the adjacent tissue). Preferred faces for this purpose are generally flat or planar, or have a larger radius of curvature than a circular cross-section. For example, a main sheath having an oval or elliptical cross-section can be used, with the flatter edge of the oval or ellipse positionable against the sternum or adjacent tissue. As another example, a main sheath having a rectangular or square cross-section (in each case preferably with rounded edges) would provided the desired face. Note that the face that seats along the sternum need only be present at the distal portion of the main sheath. Thus other embodiments might have a first cross-section which includes the desired face at the distal region, and a second (different) cross-section that need not extend the face at the proximal region.

Figure 7:
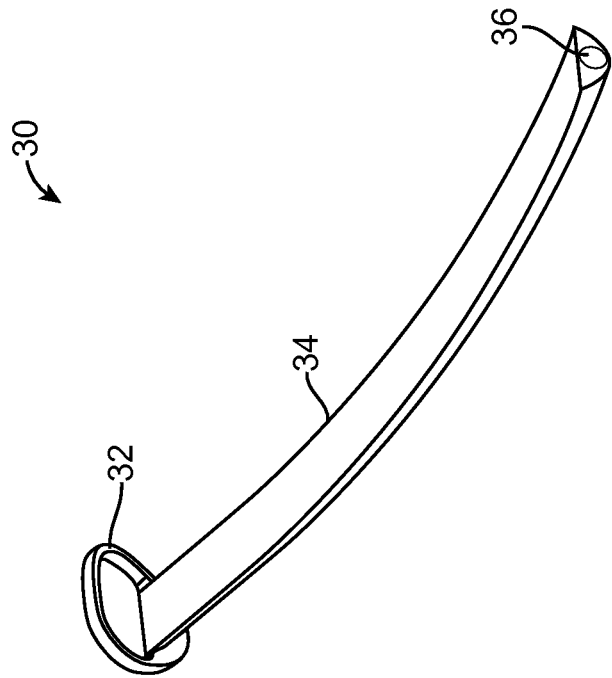
FIG. 7 is a perspective view of a channel insert for the main sheath of FIG. 6.

Each of the illustrated main sheaths 12, 12a, and 12b includes a removable channel insert 30 for receiving a scope/camera such as a flexible or (in the case of the straight sheaths) a rigid endoscope or camera. As best shown in FIG. 7, channel insert 30 includes a proximal cap 32 or ring removably engageable with the proximal end of the main sheath 12.

Figure 8:
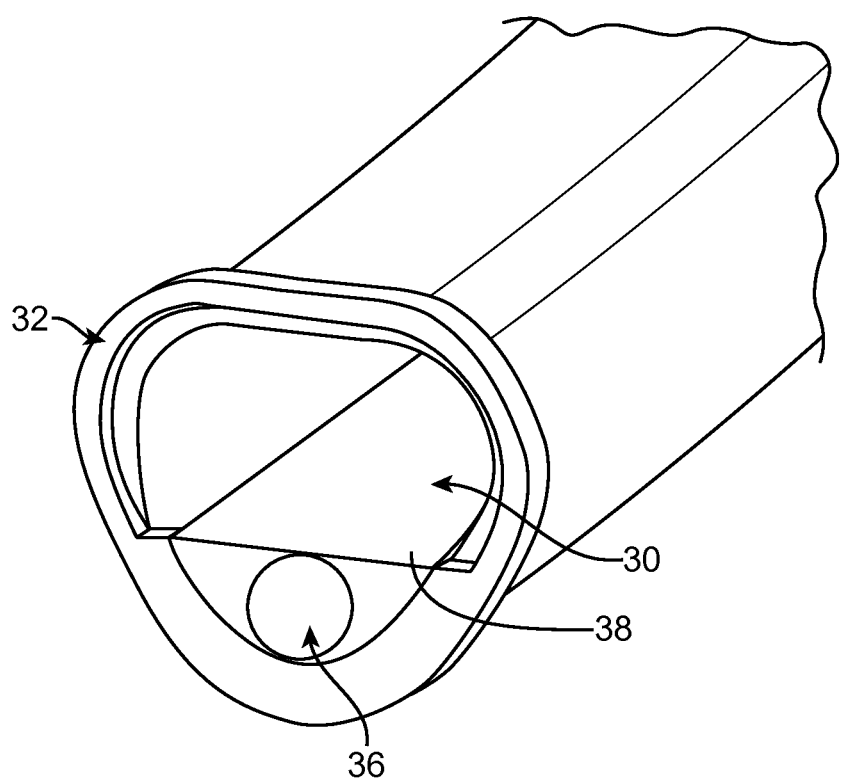
FIG. 8 is a perspective view of the distal end of the main sheath of FIG. 6, with the insert of FIG. 7 coupled to the main sheath.
Figure 9:
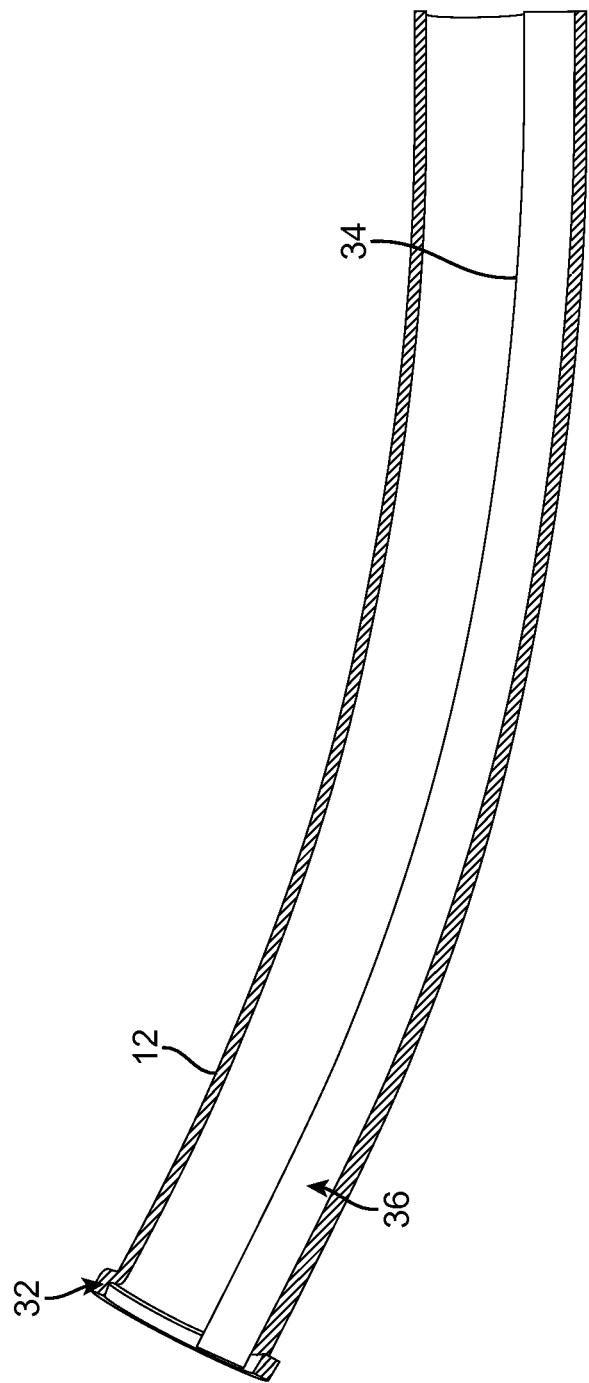
FIG. 9 is a longitudinal cross-section of the main sheath and insert assembly of FIG. 8.

A elongate member 34 extends distally from the cap 32 and includes a lumen or port 36. The lumen/port 36 is proportioned to receive a scope/camera. This arrangement allows the distal end of the scope/camera to be positioned in a stable position at the distal end of the main sheath 12. The shape of the elongate member is preferably one that will seat in a stable relationship with adjacent walls of the main sheath—for example within a corner region of the main sheath as shown in FIGS. 8, 10 and 11A-B. This position leaves the remainder of the space within the sheath available for use for the other instruments of the system. Thus the elongate member may have a generally triangular cross-section as shown in FIG. 8. The surface or wall 38 that is exposed to the interior of the main sheath (i.e. that is not in contact with a sidewall of the sheath) may be flat in its lateral dimension (or, if a straight main sheath is used, that is planar). Alternatively, referring to FIGS. 10 and 11A-B, the exposed wall 38a may have an central ridge extending longitudinally—with the contour shaped to accommodate the lumen 36—thus forming longitudinally-extending valleys extending on opposite sides of the elevated central portion. This arrangement is beneficial in that it allows instruments used through the main sheath, such as the introducer sheath 14 and the purse-string suture applier 16 (FIG. 2) to seat within the valleys during use.

In alternate embodiment, the main sheath 12, 12a, 12b includes an integrated scope channel rather than one that is removable.

Various materials are suitable for the main sheath. In some embodiments, the main sheath is rigid, and can utilize a rigid material such as stainless steel. For other embodiments, polymeric materials ranging in hardness from a stiff ABS-like material to a urethane with a hardness in Shore A scale of 40 to 100. Other suitable materials include PEEK, Delrin, Nylon, Teflon, Polyethelyne, and Polypropylene. The sheath might incorporate a lubricious lining of PTFE or other material. The sheath might be molded or extruded, with additional processing to add other features. Some designs, such as those using Pebax, might be configured to allow the physician to heat the sheath prior to use to render the sheath deformable, allowing the physical to shape the sheath to a curvature appropriate for the patient.

Similar materials as those disclosed above might also be used for the insert 30.

Obturator

Figure 5:
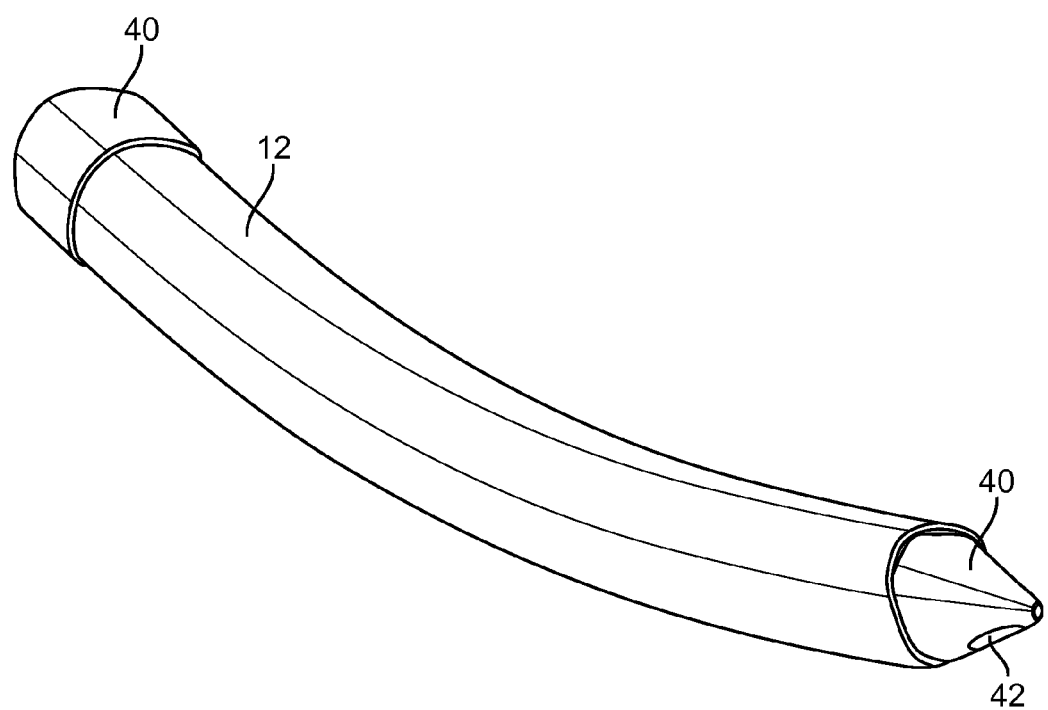
FIG. 5 is a perspective view of an exemplary main sheath for the access system, with an obturator extending through the lumen of the main sheath.

Referring to FIG. 5, an obturator 40 is provided for use during advancement of the main sheath 12 through body tissue towards the aorta. The obturator 40 is proportioned to fit within the lumen of the main sheath 12. A camera/scope lumen 42 in the obturator allows use of a scope or camera to observe the anatomy surrounding the obturator during advancement.

Figure 4:
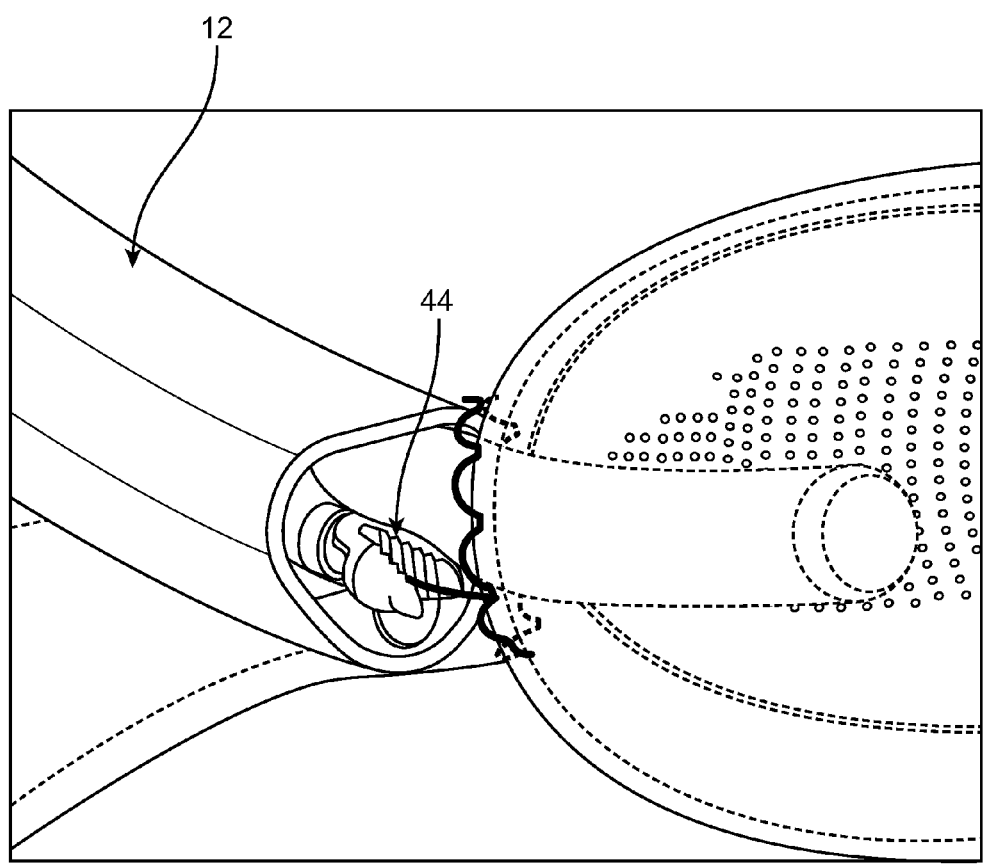
FIG. 4 is similar to FIG. 3, but shows the introducer sheath positioned through an opening formed in the wall of the ascending aorta.

In the FIG. 4 embodiment, the insert 30 is not used simultaneously with the obturator 40, although in other embodiment these two components may be proportioned for simultaneous use within the main sheath, in which case the obturator may be provided without the lumen 42.

Purse-String Suture Applier

Figure 12:
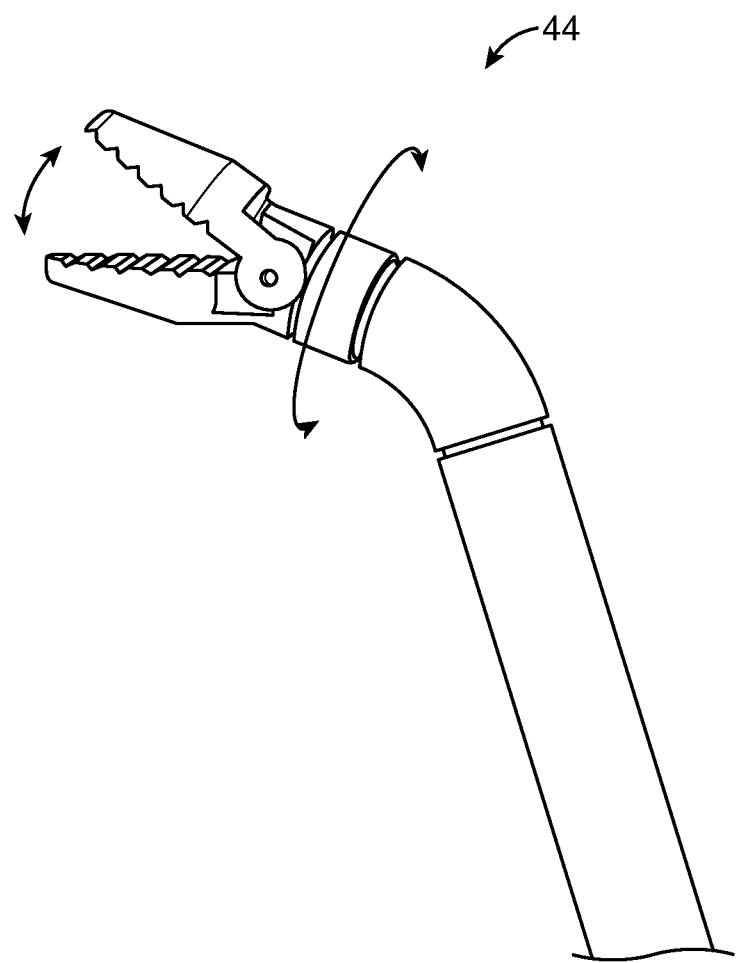
FIG. 12 is a perspective view of the distal portion of an exemplary articulating purse-string suture applier/needle holder.
Figure 13B:
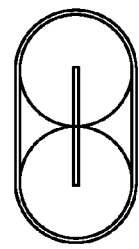
FIGS. 13A-D show a side elevation view, distal plan view, top plan view, and perspective view, respectively, of a dual dissection balloon.
Figure 13D:
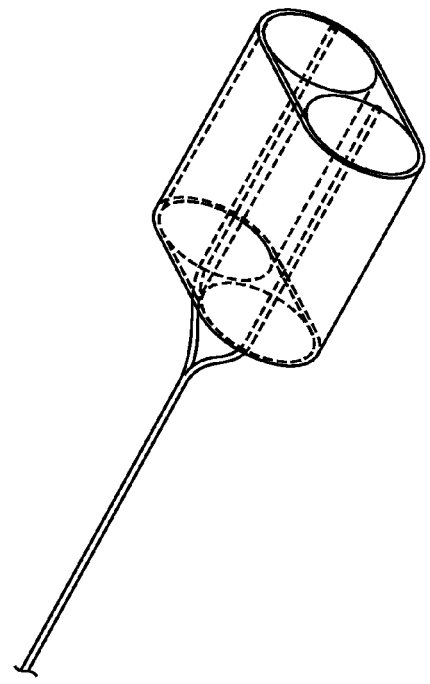
Figure 13A:
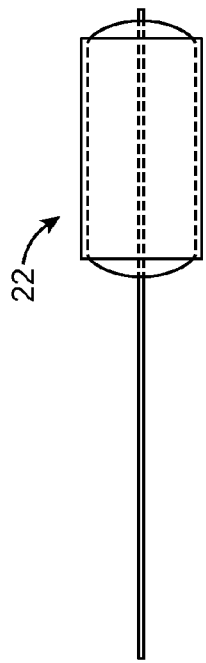
Figure 13C:
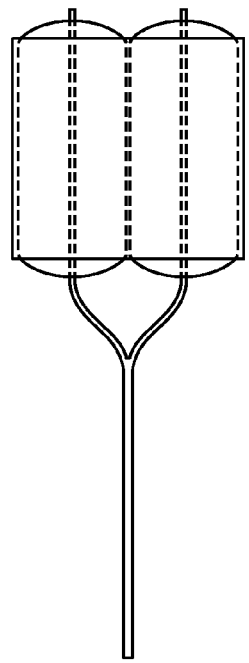

FIG. 12 shows one example of a purse-string suture applier 16. This suture applier is in the form of an articulating needle holder 44 having an end effector, in the form of a pair of jaws, supported by a shaft. The jaws are configured for holding a suture needle. The distal end of the shaft may be configured to allow axial rotation of the end effector relative to the shaft through manipulation of a manual actuator at a handle (not shown) of the suture applier. The distal end of the shaft might also include an articulation joint operable through manipulation of articulation actuators positioned at the handle. The needle holder 44 is extendable through the main sheath 12. It has features allowing the user to manipulate the jaws holding the suture needle so as to form a purse-string suture (FIG. 3) in the wall of the aorta—preferably in a manner that does not penetrate the full thickness of the vessel wall, but instead passes more shallowly (e.g. through only the adventitia of the vessel).

Another example of a purse-string suture applier 16 uses vacuum suction to engage and stabilize the outer surface of the aorta. A suture needle is then used to form the purse-string suture in the engaged and stabilized wall.

Dissection Balloons

In some instances it may be desirable to dissect tissue surrounding the incision formed at the supra-sternal notch prior to introducing the main sheath. Balloon dissectors suitable for this purpose as shown in FIGS. 13A-D and 14A-D. FIGS. 13A through 13D illustrate a dual dissection balloon 22 having a pair of elongate and/or cylindrical balloon chambers surrounded by an elastomeric membrane to form an expandable dissector with a generally oval-shaped lateral cross-section. Inflation catheters are fluidly coupled to the balloon chambers, which may be independently or simultaneously inflatable. An alternative dissection balloon 24, shown in FIGS. 14A-14C, is a single chamber balloon having a generally oval-shaped cross-section.

Needle

An instrument such as a needle (not shown) is provided for penetrating the wall of the aorta within the region encircled by the purse-string suture, so as to create an access point into the aorta. A dilator advanceable over the needle may also be provided for increasing the diameter of the penetration while minimizing blood loss.

Introducer Sheath

The system includes an introducer sheath 14 having a distal portion that is delivered through the main sheath. In use, the distal portion is passed through the needle opening (e.g. over the needle and any associated dilators) formed in the aorta, thus positioning the distal end of the introducer sheath 14 within the aorta. Instruments used to carry out the procedure within the aorta, such as an artificial aortic valve and its delivery system, are delivered to the aorta via the introducer sheath 14. For this reason, the introducer sheath 14 is constructed to maintain hemostasis despite the high rate of blood flow through the aorta.

Figure 15:
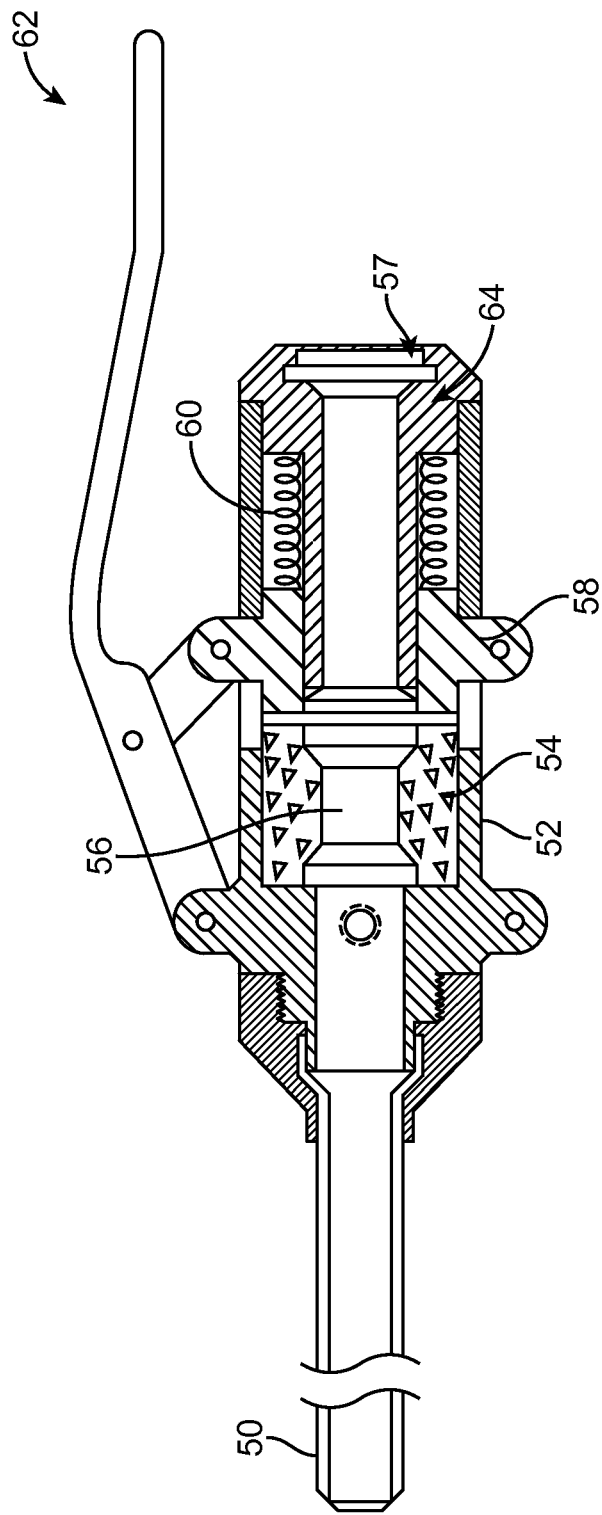
FIG. 15 is a cross-section side view of an exemplary introducer sheath. Only one handle lever is shown. The sheath is shown with the handle lever in the closed position to open the valve.

FIG. 15 shows an exemplary, prior art, introducer sheath 14, which includes a tubular shaft 50 and a valve housing 52 at the proximal end of the shaft 50. Valve 54 is disposed within the valve housing and defines an aperture 56. An instrument port 57 is located at the proximal end of the valve housing for receiving instruments to be inserted through the aperture and shaft for use within the aorta.

A slider 58 is moveable in proximal and distal directions within the valve housing 52. A spring 60 biases the slider 58 against the valve 54, compressing the valve 54 in an axial direction. Suitable springs include coil springs or wave springs.

Valve 54 is preferably made of a soft silicone material or similarly compressive material that, when axially compressed by the slider 58, will expand to fill the aperture 56, thus sealing the introducer sheath against blood loss. Because the spring 60 biases the slider 58 against the valve 54, the valve is biased in the closed position. In alternative embodiments, the spring can be positioned to bias the slider away from the valve to bias the valve in the open position.

A hard plastic material may be bonded to portions of the soft silicone. This constrains the silicone material so it cannot be pushed out of the hub of the introducer sheath.

A pair of handles 62 (one is shown) include links coupled to the slider. When the user squeezes the handles towards the valve housing 52, the links push the slider proximally against the bias of the spring, releasing some or all of the axial compression against the valve 54. With axial compression against the valve reduced, the aperture 56 opens, allowing instruments to be introduced into it, or allowing instruments already extending through it to be repositioned. When the user releases the handles, the slider returns to its biased position, compressing the valve and thus closing the aperture and causing the valve to seal around tools and instrument that are extending through it. Thus, when the valve is closed, hemostasis is maintained even with one or more devices (e.g. valve delivery system) extending through the aperture.

The introducer sheath includes features allowing the user to set a minimum diameter for the aperture opening. In the illustrated embodiment, a proximal cap 64 is engaged by threads to valve housing 52. Rotating the cap 64 in a first direction advances the cap distally relative to the valve housing, and thus limits the travel of the spring—setting a stopping point for the valve. This allows the user to pre-set the size the aperture will assume when the handles are released. This can allow the clinician to automatically apply, in a hands-free manner, a state where the valve seals down on a given diameter instrument or set of instruments with enough pressure to maintain hemostasis but minimize the drag on the inserted objects.

The introducer sheath may additionally include features allowing the user to articulate or bend the shaft 50 in one or more directions. For example, one or more tensioning elements (not shown) such as pull cables may extend through lumen in the walls of the shaft 50. In such an embodiment, the tensioning elements are coupled to one or more actuators on the proximal end of the introducer sheath, allowing the user to bend the shaft 50 through manipulation of the actuator. In some embodiments, the shaft 50 may be reinforced using a coil or braid mad of NiTi of other materials, so as to maintain radial crush strength and kink resistance at thin-wall dimensions.

Embolic Protection Device

Figure 16:
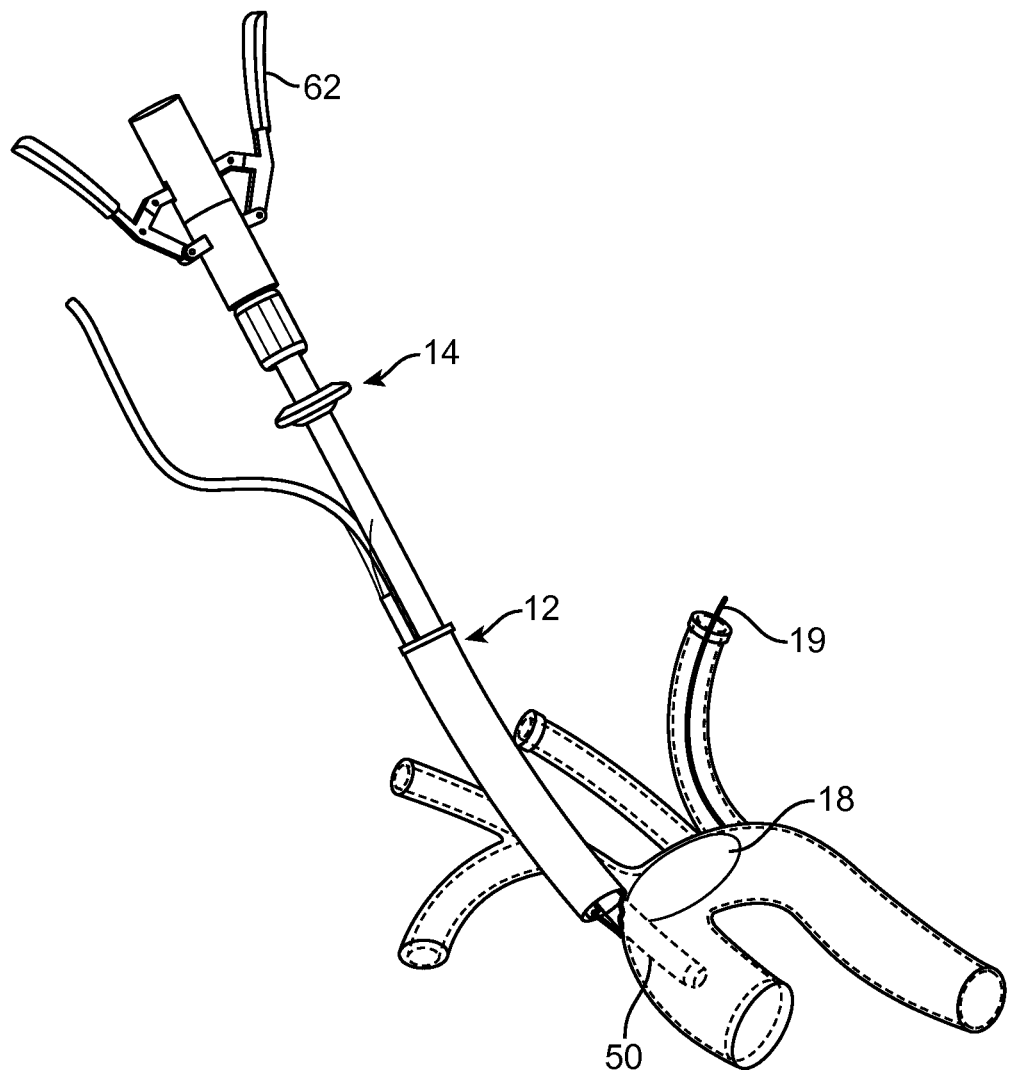
FIG. 16 is similar to FIG. 2, and more clearly shows an embolic protection device in use, with the tethering wire extending through the left subclavian artery and the barrier covering the ostia of the brachiocephalic artery and the left common carotid artery.

Referring to FIG. 16, an embolic protection device 18 may take the form of a shield positionable over the target ostia (i.e. the ostia of the brachiocephalic and left common carotid arteries, and optionally that of the left subclavian artery). The illustrated embodiment is formed of a flexible frame defining an open area. A barrier is supported by the perimeter of the frame. The barrier is one that will prevent passage of emboli through the frame, but at least certain regions of the barrier are porous so as to allow allowing blood to flow through it. In one embodiment, the porous barrier may be formed of porous silicone or polyurethane, or other materials such as woven materials. In one embodiment, the covering may be applied using dip, molding and/or spray techniques. The barrier preferably contacts the full inner perimeter of the frame, but in some embodiments the outer perimeter of the frame may be formed to be free of the barrier material to facilitate sliding of the diverter within the delivery and removal catheter(s). The frame is preferably made of nitinol or similar material, and is shape set to the desired shape.

The embolic protection device may be formed to have a variety of shapes. In the illustrated embodiment, the frame and barrier define a generally oval shape. The curvature is selected to approximately track the curvature of the portion of the aortic wall along which the target ostia are position, e.g. the surface of the barrier that faces into the aortic arch is concave, and the surface contacting the wall of the aorta and covering the ostia is convex—positioning the barrier away from the lumen of the aortic arch to avoid obstructing flow of blood through the arch.

A tethering wire or catheter support 19 for the embolic protection device extends from the proximal end of the frame as shown. In one method of using the third embodiment, the embolic protection device is positioning using access through the left subclavian artery as shown, leaving unimpeded access to the aortic valve by instruments being introduced through the introducer sheath. In another method, the embolic protection device is positioned using percutaneous access through a femoral artery, with the embolic protection device advanced through the descending aorta to the target ostia. Additional details of embolic protection devices suitable for use with the disclosed system are shown and described in U.S. Provisional application Ser. No. 13/773,625, filed Feb. 21, 2013, entitled Embolic Protection System and Method for Use in an Aortic Arch, which is incorporated herein by reference.

The disclosed system may be packaged together with instructions for use instructing the user to position and use the access system in accordance with the method described herein.

Method

In preparation for the procedure within the aorta, the embolic protection device 18 is deployed over the ostia of the head vessels such that any debris or other embolic material released during the procedure is diverted away from the brain. Deployment of the embolic protection device is described here as the first step in the process, although it should be understood that it may come later in the process, such as following positioning of the introducer sheath within the aorta.

The embolic protection device 18 is disposed within a catheter and introduced into the vasculature through an access port into the left subclavian artery, with the tethering wire 19 extending out of the body. The distal end of the catheter is advanced into the aorta and positioned with its distal opening upstream of the brachiocephalic artery. The embolic protection device is deployed from the catheter, thus covering the brachiocephalic artery and the left common carotid artery with the porous barrier.

In an exemplary method for using the remaining components of the system, an incision (e.g. approximately % inch) is formed through the skin just above the suprasternal notch. A tunnel is formed behind the sternum using a gloved finger. If needed, balloon dilators of FIGS. 13A-D or 14A-D are used to expand the tunnel formed in the tissue.

The obturator 40 is placed within the main sheath 12, and a scope or camera is passed through the scope/camera lumen 42 of the obturator. The distal end of the main sheath/obturator assembly is introduced into the incision and advanced to position the main sheath 12 behind the sternum and to position the distal end of the sheath in proximity to the aorta. Face 26 of sheath 12 is preferably seated against the surface of the sternum—such as against the posterior surface of the manubrium. The camera/scope is used during positioning of the main sheath 12 to ensure proper placement adjacent to the aorta without causing injury to the aorta.

The obturator 40 and scope/camera are withdrawn from the main sheath 12, and the scope/camera insert 30 is coupled to the main sheath 12 as shown in FIGS. 6-11. The scope/camera is positioned within the insert 30.

Figure 3:
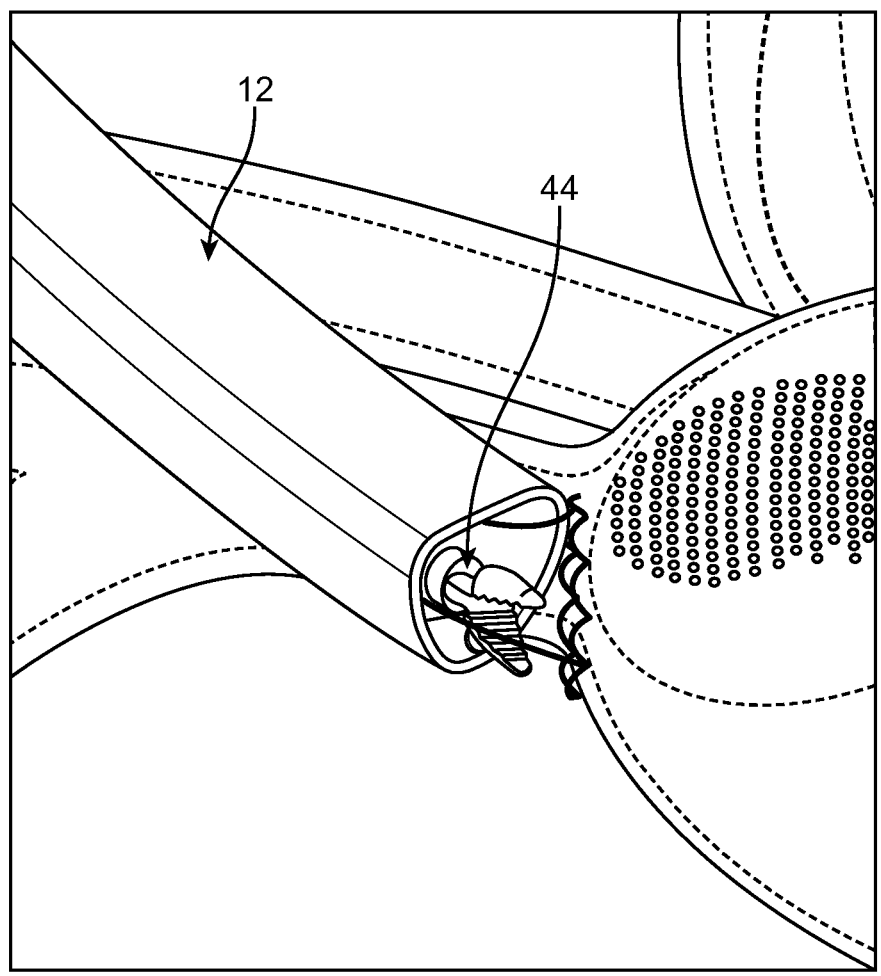
FIG. 3 is a close-up taken from with the encircled region identified as 3-3 in FIG. 2, showing placement of the purse-string suture.

Under visualization using the scope/camera, the purse-string suture applier 16 is advanced through the main sheath, and used to form a purse-string suture as shown in FIG. 3. In a preferred method for forming the purse-string suture, the suture needle is passed partially rather than fully through the vessel wall, such as only through the adventitia of the vessel.

The introducer sheath 14 is positioned adjacent to the purse-string suture applier 16 within the main sheath 12. An introducer needle is passed through the lumen of the introducer sheath 14 and used to penetrate the aorta in the region encircled by the purse-string suture, and a guidewire is advanced into the ascending aorta. Next, the distal end of the introducer sheath 14 is advanced through the needle puncture, and into the ascending aorta. For example, the introducer may be advanced over the guidewire using a dilator, which may be a staged (e.g. 9F, 18F, 28F dilator) to expand the needle puncture.

The dilator is then removed from the introducer sheath. See FIG. 4. Note that while the purse-string suture applier 16 is shown in FIG. 4, in practice the user might choose the remove it from the main sheath prior to or after the introducer sheath is positioned. The free ends of the suture may be retained outside the body (see FIG. 1) following formation of the purse-string suture ring.

The TAVI procedure is carried out through the introducer sheath 14. Articulation of the introducer sheath allows its distal portion to be optimally oriented towards the aortic valve for valve delivery.

Once the procedure is completed, the introducer sheath is withdrawn from the aorta. The purse string suture is tightened as the introducer sheath is withdrawn from the aorta, closing the puncture opening against blood loss. Finally, the main sheath 12 is withdrawn from the percutaneous incision, and the incision is then closed.

The embolic protection device is preferably removed after the main sheath has been removed. To remove the embolic protection device, a retrieval catheter or sheath is passed over the tethering wire into the aorta, and the embolic protection device is withdrawn into the retrieval catheter or sheath, causing it to collapse.

All prior patents and patent applications referred to herein, including for purposes of priority, are incorporated herein by reference.

We claim:

1. A method for performing a medical procedure using direct percutaneous access of an aorta, the method comprising:

forming an incision through skin above a suprasternal notch;

inserting a main sheath through the incision and positioning the main sheath against a posterior portion of a sternum;

forming a purse-string suture in a wall of the aorta using instruments passed through the main sheath;

forming an opening in the wall of the aorta in a region encircled by the purse-string suture;

passing a distal end of an introducer sheath through the main sheath and through the opening into the aorta;

delivering a replacement aortic valve through the introducer sheath into the aorta;

withdrawing the introducer sheath from the opening; and while withdrawing the introducer sheath, applying tension to free ends of the purse-string suture, thereby tightening the purse-string suture to close the opening.

2. The method of claim 1, wherein positioning the main sheath against a posterior portion of the sternum positions the main sheath against a posterior portion of a manubrium.

3. The method of claim 1, further including positioning an embolic protection device to divert emboli away from the ostia of at least the brachiocephalic and left common carotid arteries while allowing blood flow from the aorta into said arteries.

4. The method of claim 3, wherein positioning the embolic protection device includes percutaneously introducing the embolic protection device into a left subclavian artery or femoral artery and advancing the embolic protection device into the aorta.

5. A method for performing a medical procedure using direct percutaneous access of an aorta, the method comprising:

forming an incision through skin above a suprasternal notch;

inserting a main sheath through the incision and positioning the main sheath posterior to a sternum;

forming a purse-string suture in a wall of the aorta using instruments passed through the main sheath;

forming an opening in the wall of the aorta in a region encircled by the purse-string suture;

passing a distal end of an introducer sheath through the main sheath and through the opening into the aorta;

delivering a replacement aortic valve through the introducer sheath into the aorta;

withdrawing the introducer sheath from the opening; and closing the opening.

6. The method of claim 5, wherein positioning the main sheath includes positioning the main sheath against a posterior portion of the sternum.

7. The method of claim 6, wherein positioning the main sheath posterior to the sternum positions the main sheath against a posterior portion of a manubrium.

* * * * *